US00PP08266P

United States Patent [19]

Meilland

[11] Patent Number: Plant 8,266

[45] Date of Patent: Jun. 22, 1993

[54] ROSE PLANT—MEIHOUBA VARIETY

[75] Inventor: Alain A. Meilland, Antibes, France

[73] Assignee: The Conard-Pyle Company, West Grove, Pa.

[21] Appl. No.: 798,889

[22] Filed: Nov. 26, 1991

[51] Int. Cl.[5] ..... A01H 5/00

[52] U.S. Cl. ..... Plt./15

[58] Field of Search ..... Plt. 11, 15, 16, 22, Plt./24

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive double long-lasting blossoms which are Cream Yellow shaded with Buff Orange in coloration. The blossoms are very stable and maintain their coloration well throughout the blooming process and possess a slight fragrance. The plant exhibits an upright growth habit, forms vigorous vegetation, and is particularly well suited for cut flower production since it exhibits an excellent ability to be forced under greenhouse growing conditions. Additionally, the plant exhibits excellent disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Golden Garnette variety (U.S. Plant Pat. No. 1,898). The male parent (i.e., the pollen parent) was the Meirotervi variety (U.S. Plant Pat. No. 5,060). The parentage of the new variety can be summarized as follows:

Golden Garnette × Meirotervi.

The seends resulting from the above pollination were sown and 46 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long-lasting double blossoms which are Cream Yellow shaded with Buff Orange in coloration,
(b) forms blossoms which maintain their coloration well,
(c) forms medium green adult wood,
(d) exhibits vigorous vegetation,
(e) exhibits an upright growth habit,
(f) exhibits an excellent capacity to be forced under greenhouse conditions and is particularly well suited for cut flower production, and
(g) is not particularly affected by cryptogamic diseases.

The new variety has been found to undergo asexual propagation by a number of routes, including budding, grafting, cuttage, etc. The characteristics of the new variety have been found to be strictly transmissible by such asexual propagation from one generation to another in France and the United States.

The new variety has been named the Meihouba variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during October while budded on *Rosa indica* understock and growing in greenhouses at Cap d' Antibes, France.

DETAILED DESCRIPTION

Figures 1, 2, 3, 4, 5, 6, 7, 8, 9, 10, 11, 12, 13, 14, 15:
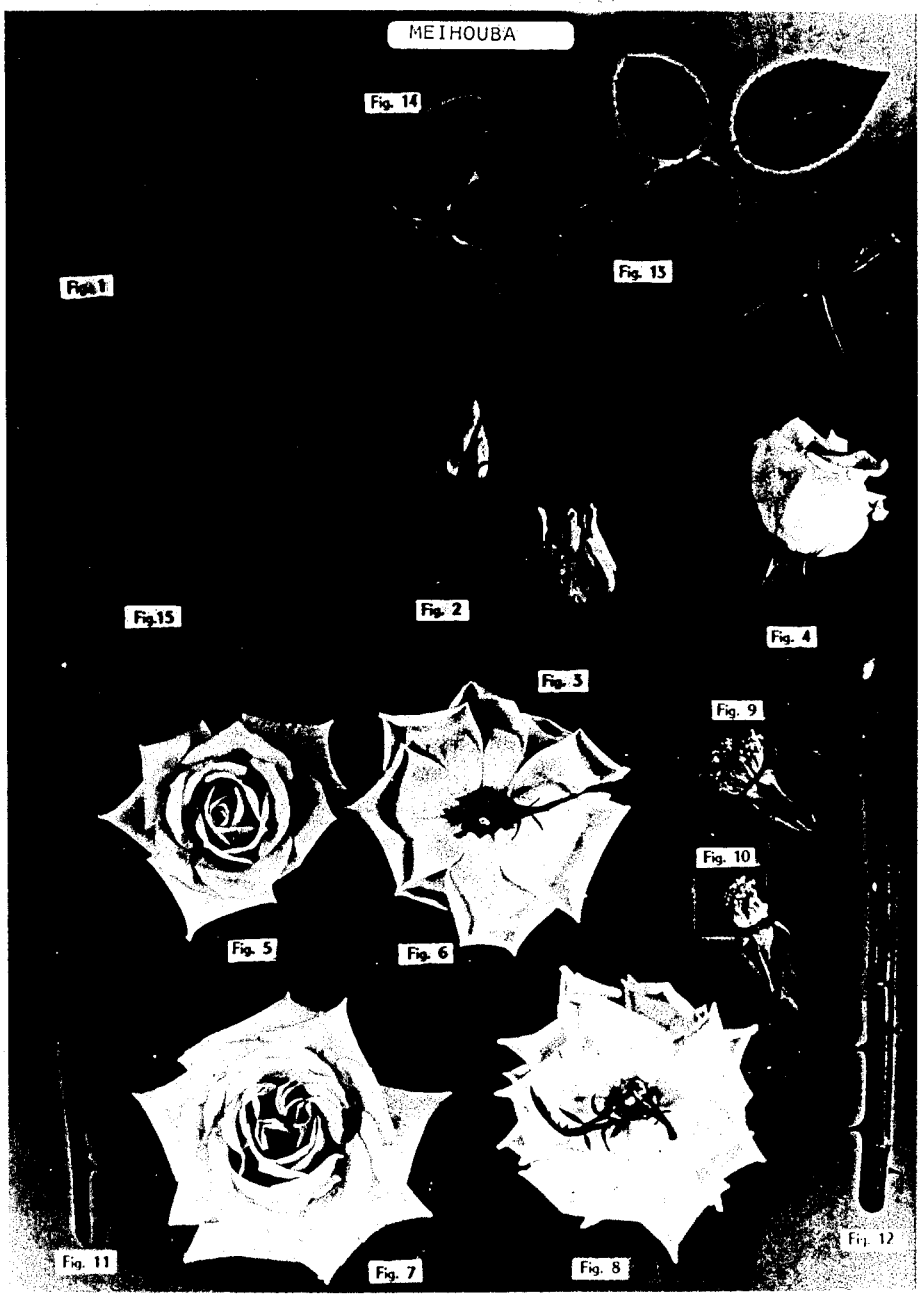
FIG. 1 illustrates a specimen of a young shoot.
FIG. 2 illustrates a specimen of a floral bud at the opening of the sepals.
FIG. 3 illustrates a specimen of a floral bud at the opening of the petals.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates a specimen of a fully open flower — plan view — obverse.
FIG. 8 illustrates a specimen of a fully open flower — plan view — reverse.
FIG. 9 illustrates a specimen of a floral receptacle showing the arrangement of the stamens and pistils.
FIG. 10 illustrates a specimen of a floral receptacle showing the arrangement of the pistils (stamens removed)
FIG. 11 illustrates a specimen of a flowering stem.
FIG. 12 illustrates a specimen of a main branch.
FIG. 13 illustrates specimens of leaves with three leaflets — plan view — upper surface (top) and lower surface (bottom)
FIG. 14 illustrates a specimen of a leaf with five leaflets — plan view — upper surface.
FIG. 15 illustrates specimens of leaves with seven leaflets — plan view — upper surface (left) and lower surface (right).

The chart used in the identification of the colors is that of The Royal Horticultural Society (R.H.S. Colour Chart). The description is based on the observation of two year old plants made during October while budded on *Rosa indica* understock and growing in greenhouses at Cap d' Antibes, France. The coloration in common terms precedes reference to the chart.

Class: Hybrid Tea.

Plant:

*Height.*—When plants are cut to a height of 85 cm., flowering stems having lengths of approximately 40 to 70 cm. commonly are formed. When grown outdoors at Wasco, Calif. at the end of one growing season, the plants commonly have a height of approximately 120 to 130 cm.

*Habit.*—Upright.

Branches:

*Color.*—Young stems: lettuce green, Yellow-Green Group 144A, more or less suffused with reddish coloration. Adult wood: medium green,, Yellow-Green Group 146B.

Thorns.—Size: small. Quantity: average. Color: reddish on young stems and greenish-pink changing to tan on mature wood.

Leaves:

*Stipules.*—Adnate, pectinate, narrow and linear.

Petioles.—Upper surface: striped reddish brown on young foliage and light green on mature foliage, and bear numerous pediculate glands. Under surface: light green, and bear very few prickles.

*Leaflets.*—Number: 3, 5, and 7. Shape: spear-shaped. Serration: single and regular. Texture: consistent. General appearance: dense, and semi-matte foliage. Color: (young foliage): Upper surface: lettuce green, Yellow-Green Group 144A, edged and more or less suffused with reddish brown coloration. Under surface: light green, Yellow-Green Group 147C, very widely stained with reddish coloration. Color: (adult foliage): Upper surface: dark green, Green Group 137A. Under surface: light green, Green Group 138B.

Inflorescense:

*Number of flowers.*—Usually one single bloom per stem.

*Peduncle.*—Straight, rigid, medium green and more or less glandular. The length is approximately 12 to 15 cm. on average.

*Sepals.*—Upper surface: tomentose, greenish in coloration. Under surface: light green, the outer sepals have edges which are more or less glandular and appendiculate and commonly end in a more or less developed foliar-like appendix.

*Buds.*—Shape: oblong. Length: approximately 4 cm. on average. Size: large. Color upon opening: Upper surface: Barium Yellow, Yellow Group 11B. Under surface: Barium Yellow, Yellow Group 11B.

*Flower.*—Shape: cup-like with parallel sides, double. Diameter: approximately 11 to 12 cm. on average. Color (when opening begins): Upper surface: Cream Yellow, Yellow Group 11C, shaded with Buff Orange, Yellow-Orange Group 22C, on the inner petals, and somewhat lighter on the outer petals. Under surface: Cream Yellow, Yellow Group 11C, shaded with Buff Orange, Yellow-Orange Group 22C, on the inner petals, and somewhat lighter on the outer petals. Color (when blooming): Upper surface: light Cream Yellow, Yellow Group 11D on the outer petals, and Cream Yellow, Yellow Group 11C, shaded with Buff Orange, Yellow-Orange Group 22C, on the inner petals. Under surface: light Cream Yellow, Yellow Group 11D, on the outer petals, and Cream Yellow, Yellow Group 11C, shaded with Buff Orange, Yellow-Orange Group 22C, on the inner petals. Color (at end of opening): Upper surface: Light Cream Yellow, Yellow Group 11D, on the outer petals, and Cream Yellow, Yellow Group 11C, shaded with Buff Orange, Yellow-Orange Group 22C, on the inner petals. Under surface: Light Cream Yellow, Yellow Group 11D, on the outer petals, and Cream Yellow, Yellow Group 11C, shaded with Buff Orange, Yellow-Orange Group 22C, on the inner petals. Fragrance: slight. Lasting quality: long, commonly approximately 7 to 9 days when cut and placed in a vase. Petal number: approximately 32 on average. Petal shape: oval. Texture: consistent. Petal drop: good. Stamen number: approximately 70 on average. Anthers: normal, yellow edged with ochre in coloration, and commonly located below the pistils. Filaments: straw yellow in coloration, and of irregular heights. Pistils: approximately 41 on average. Stigmas: normal, straw colored. Styles: fuschia with a straw-colored base, very tomentose near the base, and of irregular heights. Receptacle: medium green in coloration, and in longitudinal section it is wide and in the shape of a funnel at the dehiscence of the anthers.

Development:

*Vegetation.*—Vigorous.

*Blooming.*—Abundant.

*Resistance to diseases.*—Excellent. *Aptitude to be forced.*—Excellent.

I claim:

1. A new and distinct variety of Hybrid Tea rose plant characterized by the following combination of characteristics:

(a) forms in abundance attractive long-lasting double blossoms which are Cream Yellow shaded with Buff Orange in coloration,
(b) forms blossoms which maintain their coloration well,
(c) forms medium green adult wood,
(d) exhibits vigorous vegetation,
(e) exhibits an upright growth habit,
(f) exhibits an excellent capacity to be forced under greenhouse conditions and is particularly well suited for cut flower production, and
(g) is not particularly affected by cryptogamic diseases;

substantially as herein shown and described.

* * * * *

MEIHOUBA